(12) United States Patent
Bonnert et al.

(10) Patent No.: US 7,071,193 B2
(45) Date of Patent: Jul. 4, 2006

(54) 7-AMINO-2-ALKYLTHIOPTERIDIN-4-YL-AMINES FOR THE TREATMENT OF CHEMOKINE-RELATED DISEASES

(75) Inventors: Roger Bonnert, Charnwood (GB); Iain Walters, Charnwood (GB)

(73) Assignee: AstraZeneca AB (SE)

( * ) Notice: Subject to any disclaimer, the term of this patent is extended or adjusted under 35 U.S.C. 154(b) by 121 days.

(21) Appl. No.: 10/399,570

(22) PCT Filed: Oct. 16, 2001

(86) PCT No.: PCT/SE01/02265

§ 371 (c)(1),
(2), (4) Date: Jul. 31, 2003

(87) PCT Pub. No.: WO02/32507

PCT Pub. Date: Apr. 25, 2002

(65) Prior Publication Data

US 2004/0102447 A1    May 27, 2004

(30) Foreign Application Priority Data

Oct. 20, 2000   (SE)   .................................... 0003828

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| C07D 239/00 | (2006.01) |

(52) U.S. Cl. ...................................... 514/249; 544/259
(58) Field of Classification Search ................ 544/259; 514/249
See application file for complete search history.

(56) References Cited

U.S. PATENT DOCUMENTS

| | | |
|---|---|---|
| 2,924,472 A | 2/1960 | Bush |
| 3,182,062 A * | 5/1965 | Pachter et al. .............. 260/250 |
| 3,318,900 A | 5/1967 | Janssen |
| 3,445,120 A | 5/1969 | Barr |
| 4,061,459 A | 12/1977 | Parmann |
| 4,126,689 A | 11/1978 | Sanczuk et al. |
| 4,188,040 A | 2/1980 | Wolf et al. |
| 4,213,619 A | 7/1980 | Arlt et al. |
| 4,234,199 A | 11/1980 | Moncaster et al. |
| 4,278,677 A | 7/1981 | Nedelec et al. |
| 4,410,528 A | 10/1983 | Teranishi et al. |
| 4,483,544 A | 11/1984 | Faerber et al. |
| 4,641,858 A | 2/1987 | Roux |
| 5,064,207 A | 11/1991 | Bengtsson |
| 5,169,161 A | 12/1992 | Jones |
| 5,297,824 A | 3/1994 | Imhof et al. |
| 5,521,197 A | 5/1996 | Audia |
| 5,599,028 A | 2/1997 | Neumann et al. |
| 5,826,887 A | 10/1998 | Neumann et al. |
| 5,988,695 A | 11/1999 | Corbett, Jr. |
| 6,142,484 A | 11/2000 | Valls, Jr. |
| 6,172,067 B1 | 1/2001 | Ito et al. |
| 6,248,755 B1 | 6/2001 | Chapman et al. |
| 6,329,381 B1 | 12/2001 | Kurimoto et al. |
| 6,407,121 B1 | 6/2002 | Nagamine et al. |
| 6,432,981 B1 | 8/2002 | Finke et al. |
| 6,790,854 B1 | 9/2004 | Tsushima et al. |
| 6,958,343 B1 | 10/2005 | Bonnert et al. |
| 6,958,344 B1 | 10/2005 | Bonnert et al. |

FOREIGN PATENT DOCUMENTS

| | | |
|---|---|---|
| DE | 2331223 | 1/1974 |
| DE | 41 19 767 A1 | 12/1992 |
| EP | 0 293 078 A1 | 11/1988 |
| EP | 0 447 324 A1 | 9/1991 |
| EP | 0 778 277 A1 | 6/1997 |
| EP | 1 069 124 B1 | 1/2001 |
| EP | 1 122 257 A1 | 8/2001 |
| GB | 1009477 | 11/1965 |
| GB | 2359079 A | 8/2001 |
| JP | 51-88994 | 8/1976 |

(Continued)

OTHER PUBLICATIONS

Pachter and Nemeth, "Pteridines. I. Synthesis of Some 6-alkyl-7-amino-pteridines from Ntirosopyrimidines" Journal of Organic Chemistry, vol. 28, pp. 1187-1191 (1963).*

(Continued)

*Primary Examiner*—James O. Wilson
*Assistant Examiner*—Zachary C. Tucker
(74) *Attorney, Agent, or Firm*—Fish & Richardson P.C.

(57) ABSTRACT

Pteridine compounds of formula (I)

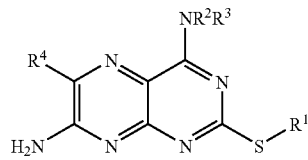

processes and intermediates used in their preparation, pharmaceutical compositions containing them and their use in the treatment of inflammatory diseases such as psoriasis, rheumatoid arthritis, diseases in which angiogenesis is associated with raised CXCR2 chemokine levels (diabetic retinopathy) and COPD. The compounds are ligands for chemokine receptors and medical indications mentioned in the description include: diseases of the respiratory tract (COPDD, asthma, bronchitis, rhinitis, fibroid lung, pneumonia, etc.), diseases of the bones and joints (arthritis, etc.), skin-diseases (psoriasis, etc), diseases of the gastrointestinal tract, diseases in other tissues and systemic disease (multipe sclerosis, atherosclerosis, AIDS, type 1 diabetes, leprosy, sepsis, etc.), allograft rejection, cancers, cystic fibrosis, stroke, burn wounds, skin ulcers, reproductive disease and more.

9 Claims, No Drawings

FOREIGN PATENT DOCUMENTS

| WO | WO 97/22596 | 6/1997 |
|----|-------------|--------|
| WO | WO 97/30035 | 8/1997 |
| WO | WO 97/32856 | 9/1997 |
| WO | WO 97/40035 | 10/1997 |
| WO | WO 98/08847 | 3/1998 |
| WO | WO 98/13354 | 4/1998 |
| WO | WO 98/25617 | 6/1998 |
| WO | WO 99/02166 | 1/1999 |
| WO | WO 99/04794 | 2/1999 |
| WO | WO 99/17773 | 4/1999 |
| WO | WO 99/36421 | 7/1999 |
| WO | WO 99/51608 | 10/1999 |
| WO | WO 00/08013 | 2/2000 |
| WO | WO 00/09511 | 2/2000 |
| WO | WO 00/38680 | 7/2000 |
| WO | WO 00/39129 | 7/2000 |
| WO | WO 00/40529 | 7/2000 |
| WO | WO 00/41669 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 01/25242 | 4/2001 |
| WO | WO 01/58902 | 8/2001 |
| WO | WO 01/58906 | 8/2001 |
| WO | WO 01/58907 | 8/2001 |
| WO | WO 01/62758 | 8/2001 |
| WO | WO 01/92224 | 12/2001 |
| WO | WO 02/04434 | 1/2002 |
| WO | WO 02/08213 | 1/2002 |
| WO | WO 02/083693 | 10/2002 |
| WO | WO 03/024966 | 3/2003 |
| WO | WO 04/026835 | 4/2004 |
| WO | WO 04/026880 | 4/2004 |

OTHER PUBLICATIONS

Vippagunta et al, "Crystalline Solids" Advanced Drug Delivery Reviews, vol. 48, pp. 3-26 (2001).*

Gavezzotti, "Are Crystal Structures Predictable?" Accounts of Chemical Research, vol. 27, pp. 309-314 (1994).*

Spickett and Timmis, "The Synthesis of Compounds with Potential Antic-folic Acid Activity. Part I. 7-Amino- and 7-Hydroxy-pteridines" Journal of the Chemical Society, pp. 2887-2895 (1954).*

Weinstock et al, "Pteridines. XII. Structure-Activity Relationships of Some Pteridine Diuretics" Journal of Medicinal Chemistry, vol. 11(3), pp. 573-579 (1968).*

Hagmann et al, "Section IV: Immunology, Endocrinology and Metabolic Diseases" Annual Reports in Medicinal Chemistry, vol. 38, pp. 191-200 (2000).*

Joseph Weinstock, et al., "Structure-Activity Relationships of Some Pteridine Diuretics," J. Med. Chem, vol. 11, No. 3, pp. 573-579 (Jan. 6, 1968).

Chemcasts, Accession No. 2001:1442861, "4,7-Pteridinediamine, 9-phenyl-2-[(phenylmethyl)thio]-," CAS Registry 343347-55-7 (Jul. 1, 2001).

CAPLUS, Accession No. 2000:76301, Document No. 132:98128, "Antiinflammatory and analgesic capsules containing betamethasone, vitamin B6, dihydrochlorothiazide and triamterene". (2000).

Ahmed et al., "Novel synthesis of 1-aryl-9-alkyl-2,3,3a,4,9,9a-hexahydro-1H-pyrrolo[2,3-b]quinoxalines by lithium aluminum hydride reduction of N-phenyl-1-benzimidazolylsuccinimides", CAPLUS 79:92106 (1973).

Baly et al., "Biological Assays for C-X-C Chemokines", Methods in Enzymology 287:69-88 (1997).

Chemical Abstracts, vol. 54, No. 10, May 1960, Abstract No. 9933f, C. Wayne Noell and Roland K. Robins, "Potential Purine Antagonists XVII. Synthesis of 2-methyl and 2-methylthio-6, 8-disubstituted purines", see Formula III when R-SMe, R1=C1, R2=OH.

Cohen et al., "Cytokine Function: A study in biologic diversity", CAPLUS 125:31527 (1996).

Cowley et al., "Preparation of 1-(3-phenyloxypropyl)piperdine derivatives as opioid receptor ligands", CAPLUS 138:39189 (2002).

Finke et al., "Preparation of piperidinylmethylcyclopentanes as modulators of CCR-5 and/or CCR-3 chemokine receptors", CAPLUS 134:56576 (2000) CAS Listing, 77 answers.

Fukuda et al., "Preparation of benzotriazole derivatives as cardiovascular agents and antipsychotics", CAPLUS 123:340149 (1995).

Gewald et al., "New Synthesis of Substituted 4-Amino-quinazolines and Their Heteroanaloga", *J. prakt. Chem.* 338:206-213 (1996).

Grant, "University of Minnesota—Twin Cities Campus College of Pharrmacy, Annual Report", [online] 1999, [retrieve on Feb. 13, 2003]. Retrieved from the internet, http://www.msi.umn.edu/general/Reports/ar99/departments/pharmacy.html.

Kiriasis et al., "Synthesis and Properties of New Pteridine Nucleosides", *Dev. Biochem.* 4:49-53 (1978).

Lee et al., "Characterization of Two High Affinity Human Interleukin-8 Receptors", *J. Biol. Chem.* 267:16283-16287 (1992).

McNaught et al., "IUPAC Compendium of Chemical Terminology, 2$^{nd}$ Ed" (1997).

Merritt et al., "Use of fluo-3 to measure cytosolic $Ca^{2+}$ in platelets and neutrophils: Loading cells with a dye, calibration of traces, measurements ini the presence of plasma, and buffering of cytosolic $Ca^{2+}$", *Biochem. J.* 269:513-519 (1990).

Ott et al., "4-amino-7, 8-dihydro-2-(methylmercapto(-8-β, -D-ribofuranosylpteridin-7-One. Modified Fusion Reaction with Trimethylsilylated Pteridine Derivatives", *Nucl. Acid. Chem.* 2:735-739 (1978).

Ott et al., "Zur Synthese des 4-Amino-7-oxo-7, 8-dihydropteridin-N-8-β-D-ribofuranosids—ein strukturanaloges Nucleosid des Adenosins", *Chem.Ber.* 107:339-361 (1974).

Patent Abstracts of Japan, abstract of JP-5-202047 A (Chugai Pharmaceut. Co. Ltd.) Aug. 10, 1993.

Sato et al., "Psychotropic agents. 3. 4-(4-Substituted piperidinyl)-1-(4-flurophenyl)-1-butanones with potent neuroleptic activity", CAPLUS 89:208915 (1978).

Taylor et al., "Molecular Determinants for Recognition of RU 24969 Analogs at Central 5-Hydroxytryptamine Recognition Sites: Use of a Bilinear Function and Substituent Volumes to Describe Steric Fit," *Molecular Pharmacology* 32:42-53 (1988).

Teranishi et al., "Piperidine derivatives and pharmaceutical compositions and pharmaceutical compositions containing them", CAPLUS 95:132947 (1981).

Trivedi et al., *Annual Reports in Medicinal Chemistry* 35:191-200 (2000).

Vandenberk et al., "1-(Benzazolylalkyl)piperidines and their salts with acids", CAPLUS 87:23274 (1977).

Vartanyan et al., "Synthesis and biological activity of 1-substituted benzimidazole and benztriazole derivatives", CAPLUS 98:4503 (1983).

West, "Solid State Chemistry and its applications", Wiley, New York, pp. 358 & 365 (1988).

* cited by examiner

7-AMINO-2-ALKYLTHIOPTERIDIN-4-YL-AMINES FOR THE TREATMENT OF CHEMOKINE-RELATED DISEASES

The present invention relates to certain thiazolopyrimidine compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3, CXCR4 and CX3CR1. These receptors represent good targets for drug development since agents which modulate these receptors would be useful in the treatment of disorders and diseases such as those mentioned above.

In accordance with the present invention, there is therefore provided a compound of formula (I) or a pharmaceutically acceptable salt or solvate thereof:

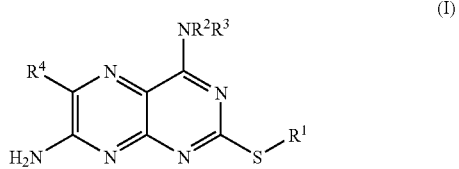

(I)

in which $R^1$ represents a $C_3$–$C_7$ carbocyclic, $C_1$–$C_8$ alkyl, $C_2$–$C_6$ alkenyl or $C_2$–$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or an aryl or heteroaryl group, both of which may be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$–$C_6$ alkyl or trifluoromethyl groups;

$R^2$ and $R^3$ each independently represent a hydrogen atom, or a $C_3$–$C_7$ carbocyclic, $C_1$–$C_8$ alkyl, $C_2$–$C_6$ alkenyl or $C_2$–$C_6$ alkynyl group, the latter four groups may be optionally substituted by one or more substituent groups independently selected from:

(a) halogen atoms, —$OR^4$, —$NR^5R^6$—$CONR^5R^6$, —$COOR^7$, —$NR^8COR^9$, —$SR^{10}$, —$SO_2R^{10}$, —$SO_2NR^5R^6$, —$NR^8SO_2R^9$;

(b) a 3–8 membered ring optionally containing one or more atoms selected from O, S, $NR^8$ and itself optionally substituted by $C_1$–$C_3$-alkyl or $OR^4$; (remove halogen;)

(c) an aryl group or heteroaryl group each of which may be optionally substituted by one or more substituents independently selected from halogen atoms, cyano, nitro, —$OR^4$, —$NR^5R^6$, —$CONR^5R^6$, —$NR^8COR^9$, —$SO_2NR^5R^6$, —$NR^8SO_2R^9$, $C_1$–$C_6$ alkyl and trifluoromethyl groups;

$R^4$ represents hydrogen, $C_1$–$C_6$ alkyl or a phenyl group the latter two of which may be optionally substituted by one or more substituent groups independently selected from halogen atoms, phenyl, —$OR^{11}$ and —$NR^{12}R^{13}$ $R^5$ and $R^6$ independently represent a hydrogen atom or a $C_1$–$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^6$, —$CONR^{15}R^{16}$, —$NR^{15}COR^{16}$, —$SONR^{15}R^{16}$, $NR^{15}SO_2R^{16}$ or $C_1$–$C_6$ alkyl, itself optionally substituted by one or more substituents independently selected from halogen atoms and —$NR^{15}R^{16}$ and —$OR^{17}$ groups;

$R^{10}$ represents a hydrogen atom or a $C_1$–$C_6$-alkyl or a phenyl group, the latter two of which may be optionally substituted by one or more substituent groups independently selected from halogen atoms, phenyl, —$OR^{17}$ and —$NR^{15}R^{16}$; and each of $R^7$, $R^8$, $R^9$, $R^{11}$, $R^{12}$, $R^{13}$, $R^{14}$ $R^{15}$, $R^{16}$, $R^{17}$ independently represents a hydrogen atom or a $C_1$–$C_6$ alkyl, or a phenyl group.

In the context of the present specification, unless otherwise indicated, an alkyl or alkenyl group or an alkyl or alkenyl moiety in a substituent group may be linear or branched. Aryl groups include phenyl and naphthyl. Heteroaryl groups include 5- or 6-membered aromatic rings containing one or more heteroatoms selected from N, S, O. Examples include pyridine, pyrimidine, thiazole, oxazole, pyrazole, imidazole, thiophene and furan.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In formula (I) above, the group $R^1$ represents a $C_3$–$C_7$ carbocyclic, $C_1$–$C_8$ alkyl, $C_2$–$C_6$ alkenyl or $C_2$–$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or an aryl or heteroaryl group, both of which may be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$–$C_6$ alkyl or trifluoromethyl groups. Preferably $R^1$ is a $CH_2$ group substituted by thienyl, furyl or phenyl, each of which can be optionally substituted by one or more $C_1$–$C_6$ alkyl, $C_1$–$C_6$ alkoxy or halogen groups. Particularly advantageous compounds of formula (I) are those in which $R^1$ represents an optionally substituted benzyl group. More preferably $R^1$ represents benzyl or benzyl substituted by one or more $C_1$–$C_6$ alkyl, $C_1$–$C_6$ alkoxy or halogen atoms. Most preferably $R^1$ represents benzyl or benzyl substituted by fluoro, chloro, or benzyl di-substituted by fluoro, di-substituted by fluoro and chloro or fluoro and methoxy.

When $R^2$ and $R^3$ represent a group substituted by one or more 3–8 membered rings optionally containing one or more atoms selected from O, S or $NR^8$, examples of such groups include piperidine, pyrrolidine, piperazine and morpholine.

Preferably one of $R^2$ and $R^3$ is hydrogen and the other is $C_1$–$C_8$ alkyl substituted by hydroxy and one or more methyl or ethyl groups. More preferably one of $R^2$ and $R^3$ is hydrogen and the other is $CH(CH_3)CH_2OH$, $CH(Et)CH_2OH$, $C(CH_3)_2CH_2OH$ or $CH(CH_2OH)_2$. Most preferably one of $R^2$ and $R^3$ is hydrogen and the other is $CH(CH_3)CH_2OH$. When one of $R^2$ and $R^3$ is hydrogen and the other is $CH(CH_3)CH_2OH$ or $CH(Et)CH_2OH$ the resulting compounds of formula (I) are preferably in the form of the (R) isomer.

Preferably $R^4$ is hydrogen.

Particularly preferred compounds of the invention include:
(2R)-2-[[7-amino-2-[[(2,3-difluorophenyl)methyl]thio]-4-pteridinyl]amino]-1-propanol,
2-[[7-amino-2-[[(2,3-difuorophenyl)methyl]thio]-4-pteridinyl]amino]-1,3-propanediol,
2-[[7-Amino-2-[[(2,3-difluorophenyl)methyl]thio]-4-pteridinyl]amino]-2-methyl-1-propanol,
(2R)-2-[[7-Amino-2-[[(2,3-difluorophenyl)methyl]thio]-4-pterldinyl]amino]-1-butanol,
2-[[7-Amino-2-[[(2,3-difluorophenyl)methyl]thio]-4-pteridinyl]amino]-2-methyl-1,3-propanediol,
(2R)-2-[[7-amino-2-[(phenylmethyl)thio]-4-pteridinyl]amino]-1-propanol,
(2R)-2-[[7-amino-2-[[(2-fluorophenyl)methyl]thio]-4-pteridinyl]amino]-1-propanol,
(2R)-2-[[7-amino-2-[[(3-chloro-4-methoxyphenyl)methyl]thio]-4-pteridinyl]amino]-1-propanol,
(2R)-2-[[7-amino-2-[[(3-chlorophenyl)methyl]thio]-4-pteridinyl]amino]-1-propanol,
(2R)-2-[[7-amino-2-[[(5-methyl-2-furanyl)methyl]thio]-4-pteridinyl]amino]-1-propanol,
(2R)-2-[[7-amino-2-[(2-thienylmethyl)thio]-4-pteridinyl]amino]-1-propanol,
(2R)-2-[[7-amino-2-[[(2-fluoro-4-methoxyphenyl)methyl]thio]-4-pteridinyl]amino]-1-propanol,
(2R)-2-[[7-amino-2-[[(3-chloro-2-fluorophenyl)methyl]thio]-4-pteridinyl]amino]-1-propanol,
and their pharmaceutically acceptable salts and solvates.

According to the invention there is also provided a process for the preparation of a compound of formula (I) which comprises heating a compound of formula (II):

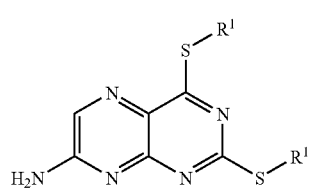

(II)

where $R^1$ is as defined in formula (I) with an amine $R^2R^3NH$. The reaction may be carried out in neat amine or in a suitable solvent such as 1-methylimidazole at a temperature between 0° C. and 150° C.

Compounds of formula (II) where $R^1$ is as defined in formula (I) may be prepared by treatment of compounds of formula (III) where $R^1$ is as defined in formula (I) with a base such as potassium hydroxide or potassium bicarbonate. The reaction may be carried out in a solvent such as a mixture of methanol and dichloromethane or NMP at a temperature between 0° C. and 100° C.

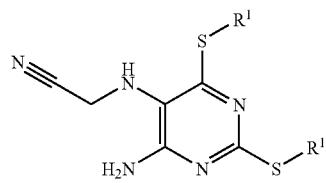

(III)

Compounds of formula (III) where $R^1$ is as defined in formula (I) and X is a halogen, may be prepared by treatment of compounds of formula (IV) where $R^1$ is as defined in formula (I) with bromoacetonitrile in the presence of a suitable base. The reaction may be carried out in a solvent such as DMSO or dioxan using diisopropylethylamine as the base at a temperature between 0° C. and 150° C.

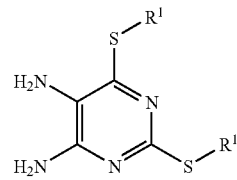

(IV)

Compounds of formula (IV) where $R^1$ is as defined in formula (I) may be prepared by treatment of a compound of formula (V) with a compound of formula $R^1X$ where $R^1$ is as defined in formula (I) above and X is a leaving group such as bromide in the presence of a base such as potassium hydroxide in a solvent such as methanol at ambient temperature.

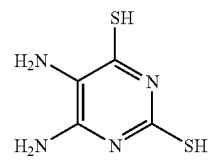

(V)

The compound of formula (V) is commercially available.

It will be appreciated by those skilled in the art that in the processes described above the functional groups (e.g. hydroxyl groups) of intermediate compounds may need to be protected by protecting groups. The final stage in the preparation of the compounds of the invention may involve the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Novel intermediate compounds form a further aspect of the invention. In particular compounds of formula (II) are novel and form an aspect of the invention.

The compounds of formula (I) above may be converted to a pharmaceutically acceptable salt or solvate thereof, either a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compounds of formula (I) have activity as pharmaceuticals, in particular as modulators of chemokine receptors, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyperresponsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; post-operative adhesions, and sepsis.

(6) (allograft rejection) acute and chronic following, for example, transplantation of kidney, heart, liver, lung, bone marrow, skin and cornea; and chronic graft versus host disease;

(7) Cancers, especially non-small cell lung cancer (NSCLC), malignant melanoma, prostate cancer and squamous sarcoma, and tumour metastasis;

(8) Diseases in which angiogenesis is associated with raised CXCR2 chemokine levels (e.g. NSCLC, diabetic retinopathy).

(9) Cystic fibrosis, stroke, re-perfusion injury in the heart, brain, peripheral limbs and other organs.

(10) Burn wounds & chronic skin ulcers

(11) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, rhumatoid arthritis, diseases in which angiogenesis is associated with raised CXCR2 chemokine levels, and COPD. It is preferred that the compounds of the invention are used to treat rhumatoid arthritis.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

(2R)-2-[[7-amino-2-[[(2,3-difluorophenyl)methyl]thio]-4-pteridinyl]amino]-1-propanol (a)  2,6-bis[[(2,3-difluorophenyl)methyl]thio]-4,5-pyrimidinediamine To a solution of potassium hydroxide powder (7.72 g) in methanol (250 ml) was added first 5,6-diamino-2,4-pyrimidinedithiol (10.9 g) followed by 2,3-difluorobenzyl bromide (22.5 g). The reaction mixture was stirred for one hour at room temperature then poured into water (500 ml), giving a brown precipitate. This was isolated by filtration, washing with isopropanol and diethyl ether, to give the subtitled compound as a pale brown solid (15.0 g).

MS (APCI) 427 (M+H, 100%).

(b)  [[4-amino-2,6-bis[[(2,3-difluorophenyl)methyl]thio]-5-pyrimidinyl]amino]acetonitrile A solution of the product of example 1 step a) (5.0 g), diisopropylethylamine (2.8 ml) and bromoacetonitrile (1.1 ml) in DMSO (50 ml) was heated at 100° C. for 5 hours. After cooling, the reaction mixture was partitioned between ethyl acetate and saturated aqueous ammonium chloride. The organic phase was dried over magnesium sulphate, filtered and evaporated to give a black oil which was purified by silica gel flash column chromatography, eluting with 10:1 dichloromethane:ethyl acetate, to give the subtitled compound as a pale orange solid (1.6 g).

MS (APCI) 466 (M+H, 100%).

NMR δH (CDCl$_3$) 7.95–7.25 (6H, m), 5.15 (2H, br s), 4.45 (2H, s), 4.39 (2H, s), 3.82 (2H, d), 2.78 (1H, t).

(c)  2,4-bis[[(2,3-difluorophenyl)methyl]thio]-7-pteridinamine

A solution of the product from example 1 step b) (1.35 g) and potassium hydroxide (114 mg) in methanol (50 ml) and dichloromethane (20 ml) was stirred at room temperature for 24 hours. After evaporation in vacuo, the residue was purified by silica gel flash column chromatography, eluting with 5:1 dichloromethane:ethyl acetate, to give the subtitled compound as a pale yellow solid (0.37 g).

MS (APCI) 463 (M+H).

NMR δH (d$_6$-DMSO) 8.13 (1H, s), 8.01 (2H , br s), 7.42–7.28 (4H, m), 7.19–7.11 (2H, m), 4.52 (2H, s), 4.49 (2H, s).

(d)  (2R)-2-[[7-amino-2-[[(2,3-difluorophenyl)methyl]thio]-4-pteridinyl]amino]-1

A solution of the product from example 1 step c) (0.2 g) in D-alaninol (2 ml) was heated at 120° C. for 30 minutes. After cooling, the reaction mixture was partitioned between ethyl acetate and saturated aqueous ammonium chloride. The organic phase was dried over magnesium sulphate, filtered and evaporated to give a brown oil which was purified by silica gel flash column chromatography, eluting with 200:10:1 dichloromethane:methanol:880 ammonia solution, to give the title compound as a pale brown solid (0.08 g).

m.p. 211–213° C.

MS (APCI) 379 (M+H, 100%).

NMR δH (d$_6$-DMSO) 7.95 (1H, s), 7.62 (1H, d), 7.43 (2H, s), 7.40 (1H, m), 7.34 (1H, m), 7.13 (1H, m), 4.82 (1H, t), 4.45 (2H, s), 4.25 (1H, m), 3.48 (2H, m), 1.15 (3H, d).

EXAMPLE 2

2-[[7-amino-2-[[(2,3-difluorophenyl)methyl]thio]-4-pteridinyl]amino]-1,3-propanediol A solution of the product from example 1, step (c) (0.12 g) and serinol (330 mg) in 1-methylimidazole (1 ml) was heated at 130° C. for 90 minutes. After cooling, the reaction mixture was partitioned between ethyl acetate and saturated aqueous ammonium chloride. The organic phase was dried over magnesium sulphate, filtered and evaporated to give a brown solid which was purified by silica gel flash column chromatography, eluting with 200:20:1 dichloromethane:methanol:880 ammonia solution, to give the title compound as a pale brown solid (0.02 g).

m.p. 251–253° C.

MS (APCI) 395 (M+H, 100%).

NMR δH (d$_6$-DMSO) 7.96 (1H, s), 7.46 (2H, s), 7.41 (1H, m), 7.30 (1H, m), 7.14 (1H, m), 4.80 (2H, t), 4.46 (2H, s), 4.20 (1H, m), 3.57 (4H, m).

EXAMPLE 3

2-[[7-Amino-2-[[(2,3-difluorophenyl)methyl]thio]-4-pteridinyl]amino]-2-methyl-1-propanaol A solution of the product from example 1, step (c) (0.25 g) in 2-amino-2-methylpropanol (2.5 ml) was heated in a microwave at 150° C. for 45 minutes. After cooling, the reaction mixture was partitioned between ethyl acetate and saturated aqueous ammonium chloride. The organic phase was dried over magnesium sulphate, filtered and evaporated to give a brown oil which was purified by silica gel flash column chromatography, eluting with 100:7 dichloromethane:methanol: and reverse phase HPLC to give the title compound as an off white solid (0.034 g).

m.p. 226–229° C.

MS (APCI) 393 (M+H, 100%).

NMR δH (d$_6$-DMSO) 7.94 (1H, s), 7.46 (2H, s), 7.40 (1H, m), 7.33 (1H, m), 7.16 (2H, m), 5.21 (1H, t), 4.46 (2H, s), 3.48 (2H, m), 1.36 (3H, d).

EXAMPLE 4

(2R)-2-[[7-Amino-2-[[(2,3-difluorophenyl)methyl]thio]-4-pteridinyl]amino]-1-butanol A solution of the product from example 1, step (c) (0.25 g) and R-2-aminobutanol (0.24 ml) in N-methylimidazole (1 ml) was heated in a microwave at 150° C. for 30 minutes. After cooling, the reaction mixture was partitioned between ethyl acetate and saturated aqueous ammonium chloride. The organic phase was dried over magnesium sulphate, filtered and evaporated to give a brown oil which was purified by silica gel flash column chromatography, eluting with 100:5 dichloromethane:methanol: and reverse phase HPLC to give the title compound as an off white solid (0.033 g).

m.p. 185–189° C.

MS (APCI) 393 (M+H, 100%).

NMR δH (d$_6$-DMSO) 7.96 (1H, s), 7.56 (1H, d), 7.40 (3H, m), 7.32 (1H, m), 7.14 (1H, m), 4.77 (1H, t), 4.44 (2H, dd), 4.11 (1H, m), 3.49 (2H, dm), 1.60 (2H, dm), 0.83 (3H, t)

EXAMPLE 5

2-[[7-Amino-2-[[(2,3-difluorophenyl)methyl]thio]-4-pteridinyl]amino]-2-methyl-1,3-propanediol A solution of the product from example 1, step (c) (0.25 g) and 2-amino-2-methyl-1,3-propanediol (0.28 ml) in N-methylimidazole (1 ml) was heated in a microwave at 160° C. for 95 minutes. After cooling, the reaction mixture was partitioned between ethyl acetate and saturated aqueous ammonium chloride. The organic phase was dried over magnesium sulphate, filtered and evaporated to give a brown oil which was purified by silica gel flash column chromatography, eluting with 10:1 dichloromethane:methanol to give the title compound as a pale brown solid (0.031 g).

m.p. 220–227° C.

MS (APCI) 409 (M+H, 100%).

NMR δH (d$_6$-DMSO) 7.95 (1H, s), 7.56 (2H, s), 7.31 (2H, m), 7.21 (1H, s), 7.15 (1H, m), 5.01 (2H, t), 4.45 (2H, s), 3.67, 3.56 (2H, 2×m), 1.32 (3H, s).

EXAMPLE 6

(2R)-2-[[7-amino-2-[(phenylmethyl)thio]-4-pteridinyl]amino]-1-propanol (a) 2,6-bis[(phenylmethyl)]thio]-4,5-pyrimidinediamine Prepared by the method of example 1, step (a), using benzyl bromide

MS (APCI) 355 (M+H, 100%).

(b) [[4-amino-2,6-bis[(phenylmethyl)thio]-5-pyrimidinyl]amino]acetonitrile

Prepared by the method of example 1, step (b), using the product from example 6, step (a)

MS (APCI) 394 (M+H, 100%).

(c) 2,4-bis[(phenylmethyl)thio]-7-pteridinamine

Prepared by the method of example 1, step (c), using the product from example 6, step (b)

MS (APCI) 390 (M+H, 100%).

(d) (2R)-2-[[7-amino-2-[(phenylmethyl)thio]-4-pteridinyl]amino]-1-propanol

Prepared by the method of example 1, step (d), using the product from example 6, step (c)

MS (APCI) 343 (M+H, 100%).

NMR δH (d$_6$-DMSO) 7.95 (1H, s), 7.58 (1H, d), 7.45–7.20 (5H, m), 4.82 (1H, t), 4.83 (1H, t), 4.38 (2H, m), 4.27 (1H, m), 3.54–3.42 (2H, m), 1.16 (3H, d).

EXAMPLE 7

(2R)-2-[[7-amino-2-[[(2-fluorophenyl)methyl]thio]-4-pteridinyl]amino]-1-propanol (a) (2R)-2-[(7-amino-2-mercapto-4-pteridinyl)amino]-1-propanol To a suspension of the product from example 6, step (d), (300 mg) in liquid ammonia (20 ml) was added sodium metal until a consistent blue colour ensued. This was then quenched with ammonium chloride powder. The solvent was allowed to evaporate and the residue taken up into water (20 ml) and the pH adjusted to 5–6 with concentrated hydrochloric acid. The product was then collected by filtration (75 mg).

MS (APCI) 253 (M+H, 100%).

(b) (2R)-2-[[7-amino-2-[[(2-fluorophenyl)methyl]thio]-4-pteridinyl]amino]-1propanol To a mixture a mixture of the product from example 7, step (a) (75 mg) in DMSO (1 ml) and Hunigs base (0.2 ml) was added 2-fluorobenzylbronide (30 ul) and the mixture stirred at room temperature for 30 mins. The mixture was poured into water (10 ml) extracted into ethyl acetate, dried and evaporated to dryness. The residue was then purified by HPLC. The above procedure was repeated and both yields combined to give the title compound as a white solid (145 mg).

MS (APCI) 361 (M+H, 100%).

NMR δH (d$_6$-DMSO) 7.96 (1H, s), 7.42 (2H, m), 7.34 (2H, s), 7.29–7.11 (3H, m), 4.83 (1H, t), 4.36 (2H, m), 4.26 (1H, m), 4.05 (2H, m), 1.16 (3H, d).

EXAMPLE 8

(2R)-2-[[7-amino-2-[[(3-chloro-4-methoxyphenyl)methyl]thio]-4-pteridinyl]amino]-1-propanol Prepared by the method of example 7, step (b), using 3-chloro-4-methoxybenzyl bromide. The product was purified by recrystallisation from acetonitrile.

MS (APCI) 407 (M+H, 100%).

NMR δH (d$_6$-DMSO) 7.95 (1H, d), 7.58 (1H, d), 7.50 (1H, d), 7.41 (2H, m), 7.05 (1H, d), 4.82 (1H, t), 4.37 (2H, m), 4.27 (1H, m), 3.82 (3H, s), 3.49 (2H, m), 1.16 (3H, d).

EXAMPLE 9

(2R)-2-[[7-amino-2-[[(3-chlorophenyl)methyl]thio]-4-pteridinyl]amino]-1-propanol Prepared by the method of example 7, step (b), using 3-chloro-benzyl bromide.

MS (APCI) 377 (M+H, 100%).

NMR δH (d₆-DMSO) 7.95 (1H, d), 7.62 (1H, d), 7.51 (1H, m), 7.41 (3H, m), 7.31 (2H, m), 4.82 (1H, t), 4.39 (2H, m), 4.26 (1H, m), 3.53–3.41 (2H, m), 1.16 (3H, d).

EXAMPLE 10

(2R)-2-[[7-amino-2-[[(5-methyl-2-furanyl)methyl]thio]-4-pteridinyl]amino]-1propanol (a) (2R)-2-[[7-amino-2-[[(2,3-difluorophenyl)methyl]sulphonyl]-4-pteridinyl]amino]-1-propanol To a suspension of the product from Example 1 (0.54 g) in acetonitrile (200 ml) was added a solution of Oxone (5.4 g) in water (200 ml) and the mixture was stirred overnight. After removing the acetonitrile by concentration, the aqueous solution was neutralised with sodium hydroxide solution and extracted with ethyl acetate. The organic extracts were dried over magnesium sulphate, filtered and concentrated to leave the subtitled compound as a brown solid (0.38 g).

MS (ESI) 411 (M+H, 100%).

(b) (2R)-2-[[7-amino-2-[[(5-methyl-2-furanyl)methyl]thio]-4-pteridinyl]amino]-1-propanol A solution of the product from example 10, step (a) (0.18 g) and 5-methyl-2-furanmethanethiol (75 mg) in anhydrous DMSO (3 ml) was treated with potassium t-butoxide solution in THF (1.0 M, 0.44 ml) and stirred at room temperature for 1 hour. The solution was purified directly by preparative reversed phase HPLC on a Waters 19×50 mm Symmetry C8 silica column eluted with 0.1% aqueous ammonium acetate:acetonitrile (70:30) to give an off-white solid that was dried under reduced pressure at 40° C. (8 mg).

MS (APCI) 347 (M+H, 100%).

NMR δH (d₆-DMSO) 7.95 (1H, s), 7.61 (1H, d), 7.40 (2H, br), 6.18 (1H, m), 5.96 (1H, s), 4.83 (1H, t), 4.37 (2H, s), 4.27 (1H, m), 3.42–3.54 (2H, m), 2.22 (3H, s), 1.17 (3H, d).

EXAMPLE 11

(2R)-2-[[7-amino-2-[(2-thienylmethyl)thio]-4-pteridinyl]amino]-1-propanol

A solution of the product from Example 10, step (a) (0.18 g) and 2-thienylmercaptan (70 mg) in anhydrous DMSO (3 ml) was treated with potassium t-butoxide solution in THF (1.0 M, 0.44 ml) and stirred at room temperature for 1 hour. The solution was purified directly by preparative reversed phase HPLC on a Waters 19×50 mm Symmetry C8 silica column eluted with 0.1% aqueous ammonium acetate:acetonitrile (70:30) to give an off-white solid that was dried under reduced pressure at 40° (20 mg).

MS (APCI) 349 (M+H, 100%).

NMR δH (d₆-DMSO) 7.96 (1H, s), 7.62 (1H, d), 7.42 (2H, br), 7.34 (1H, m), 7.08 (1H, m) 6.92 (1H, m), 4.83 (1H, t), 4.59 (2H, m), 4.29 (1H, m), 3.42–3.54 (2H, m), 1.17 (3H, d).

EXAMPLE 12

(2R)-2-[[7-amino-2-[[(2-fluoro-4-methoxyphenyl)methyl]thio]-4-pteridinyl]amino]-1-propanol Thionyl chloride (0.19 ml) was added to an ice-cold solution of 2-fluoro-4-methoxybenzenemethanol (0.188 g) in dichloromethane (10 ml) and the resulting solution was stirred for 1 hour then concentrated. The residue was dissolved in DMSO (3 ml) and N,N-diisopropylethylamine (0.35 ml) and the product from example 7, step (a) (0.252 g) were added. After stirring at room temperature overnight, the mixture was purified directly by preparative reversed phase HPLC on a Waters 19×50 mm Symmetry C8 silica column eluted with 0.1% aqueous ammonium acetate:acetonitrile (65:35) to give a pale brown powder that was dried under reduced pressure at 40° (0.173 g).

MS (APCI) 391 (M+H, 100%).

NMR δH (d₆-DMSO) 7.95 (1H, s), 7.59 (1H, d), 7.47 (1H, t), 7.41 (2H, br), 6.82 (1H, m), 6.72 (1H, m), 4.82 (1H, t), 4.33 (2H, s), 4.22–4.29 (1H, m), 3.74 (3H, s), 3.41–3.55 (2H, m), 1.17 (3H, d).

EXAMPLE 13

(2R)-2-[[7-amino-2-[[(3-chloro-2-fluorophenyl)methyl]thio]-4-pteridinyl]amino]-1-propanol (a) 2,6-bis[[(3-chloro-2-fluorophenyl)methyl]thio]-4,5-pyrimidinediamine To a solution of potassium hydroxide powder (2.5 g) in methanol (80 ml) was added first 5,6-diamino-2,4-pyrimidinedithiol (3.6 g) followed by 3-chloro-2-fluorobenzyl bromide (6.3 g). The reaction mixture was stirred for one hour at room temperature then poured into water (180 ml), giving a brown precipitate. This was isolated by filtration, washing with isopropyl alcohol and diethyl ether, to give the subtitled compound as a pale brown solid (5.4 g).

MS (APCI+ve) 459/461/463 (M+H, 100%).

(b) [[4-amino-2,6-bis[[(3-chloro-2-fluorophenyl)methyl]thio]-5-pyrimidinyl]amino]acetonitrile To a solution of the product of example 13, step (a) (4.2 g) and diisopropylethylamine (1.2 ml) in dioxan (40 ml) was added bromoacetonitrile (1.2 g) and the mixture heated at 100° C. for 23 hours. After cooling, the red reaction solution was adsorbed onto silica and purified by silica gel flash column chromatography, eluting with dichloromethane then 95:5 dichloromethane:ethyl acetate, to give the subtitled compound as a pale orange solid (3.1 g).

MS (APCI+ve) 498 (M+H, 100%).

NMR δH (d₆DMSO) 7.38–7.16 (6H, m), 6.97 (2H, br s), 4.42 (1H, s), 4.34 (4H, s), 3.86 (2H, d).

(c) 2,4-bis[[(3-chloro-2-fluorophenyl)methyl]thio]-7-pteridinamine

A solution of the product from example 13, step (b) (1.4 g) and potassium hydroxide (110 mg) in methanol (80 ml) and dichloromethane (120 ml) was stirred at room temperature for 24 hours. After evaporation in vacuo, the residue rendered the subtitled compound as a pale yellow solid (1.4 g).

MS (APCI+ve) 496/498/500 (M+H).

NMR δH (d₆-DMSO) 8.13 (1H, s), 8.02 (2H, br s), 7.46–7.17 (6H, in), 4.44 (4H, s).

(d) (2R)-2-[[7-amino-2-[[(2,3-difluorophenyl)methyl]thio]-4-pteridinyl]amino]-1propanol A solution of the product from example 13, step (c) (1.0 g) in D-alaninol (10 ml) was heated at 120° C. for 40 minutes. After cooling, the reaction mixture was partitioned between ethyl acetate and saturated aqueous ammonium chloride. The organic phase was dried over magnesium sulphate, filtered and evaporated to give a light brown solid which was purified by silica gel flash column chromatography, eluting with dichloromethane then 30:1 then 20:1 dichloromethane:methanol, to give the title compound as a pale brown solid (0.25 g).

m.p. 224–226° C.

MS (APCI) 394/396 (M+H, 100%).

NMR δH (d₆-DMSO) 7.95 (1H, s), 7.61 (1H, t), 7.56 (1H, s), 7.45 (3H, m), 7.16 (1H, t), 4.83 (1H, t), 4.34 (2H, s), 4.23 (1H, m), 3.50 (2H, m), 1.15 (3H, d).

Pharmacological Data

Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH₂PO₄), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl₂, 1 mM MgCl₂, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have IC₅₀ values of less than (<) 10 μM.

Intracellular Calcium Mobilisation Assay

Human neutrophils were prepared from EDTA-treated peripheral blood, as previously described (Baly et al. (1997) Methods in Enzymology 287 pp70–72), in storage buffer [Tyrode's salt solution (137 mM NaCl, 2.7 mM KCl, 0.4 mM NaH₂PO₄) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp513–519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM CaCl₂ and 1 mM MgCl₂. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A₅₀ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

The invention claimed is:

1. A compound of formula (I) or a pharmaceutically acceptable salt thereof:

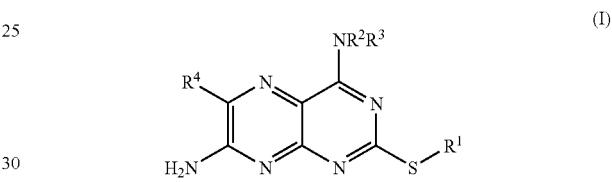

in which

R¹ represents a C₃–C₇ carbocyclic, C₁–C₈ alkyl, C₂–C₆ alkenyl or C₂–C₆ alkynyl group, each of groups being optionally substituted by one or more substituent groups independently selected from halogen atoms, —OR⁴, —NR⁵R⁶, —CONR⁵R⁶, —COOR⁷, —NR⁸COR⁹, —SR¹⁰, —SO₂R¹⁰, —SO₂NR⁵R⁶, —NR⁸SO₂R⁹ or an aryl or heteroaryl group, both of which may be optionally substituted by one or more substituents independently selected from halogen atoms, cyano, nitro, —OR⁴, —NR⁵R⁶, —CONR⁵R⁶, —COOR⁷, —NR⁸COR⁹, —SR¹⁰, —SO₂R¹⁰, —SO₂NR⁵R⁶, —NR⁸SO₂R⁹, C₁–C₆ alkyl or trifluoromethyl groups;

one of R² and R³ is hydrogen and the other is C₁–C₈ alkyl substituted by hydroxy and one or more methyl or ethyl groups, R⁴ represents hydrogen, C₁–C₆ alkyl or a phenyl group the latter two of which may be optionally substituted by one or more substituent groups independently selected from halogen atoms, phenyl, —OR¹¹ and —NR¹²R¹³

R⁵ and R⁶ independently represent a hydrogen atom or a C₁–C₆ alkyl or phenyl group the latter two of which may be optionally substituted by one or more substituent groups independently selected from halogen atoms, phenyl, —OR¹⁴ and —NR¹⁵R¹⁶, —CONR¹⁵R¹⁶, —NR¹⁵COR¹⁶, —SONR¹⁵R¹⁶, NR¹⁵SO₂R¹⁶ or R⁵ and R⁶ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —OR¹⁴, —COOR¹⁴, —NR¹⁵R¹⁶, —CONR¹⁵R¹⁶, —NR¹⁵COR¹⁶, —SONR¹⁵R¹⁶, NR¹⁵SO₂R¹⁶ or C₁–C₆ alkyl, itself optionally substituted by one or more substituents independently selected from halogen atoms and —NR$^{15}$R$^{16}$ and —OR$^{17}$ groups;

R$^{10}$ represents a hydrogen atom or a C$_1$–C$_6$-alkyl or a phenyl group, the latter two of which may be optionally substituted by one or more substituent groups independently selected from halogen atoms, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ independently represents a hydrogen atom or a C$_1$–C$_6$, alkyl, or a phenyl group.

2. A compound according to claim 1, wherein R$^1$ represents an optionally substituted benzyl group.

3. A compound according to claim 1, wherein R$^4$ is hydrogen.

4. A compound according to claim 1 selected from:
(2R)-2-[[7-amino-2-[[(2,3 -difluorophenyl)methyl]thio]-4-pteridinyl]amino]-1-propanol, 2-[[7-amino-2-[[(2,3-difluorophenyl)methyl]thio]-4-pteridinyl]amino]-1,3-propanediol, 2-[[7-Amino-2-[[(2,3-difluorophenyl) methyl]thio]-4-pteridinyl]amino]-2-methyl-1-propanol, (2R)-2-[[7-Amino-2-[[(2,3-difluorophenyl) methyl]thio]-4-pteridinyl]amino]-1-butanol, 2-[[7-Amino-2-[[(2,3-difluorophenyl)methyl]thio]-4-pteridinyl]amino]-2-methyl-1,3-propanediol, (2R)-2-[[7-amino-2-[(phenylmethyl)thio]-4-pteridinyl] amino]-1-propanol, (2R)-2-[[7-amino-2-[[(2-fluorophenyl)methyl]thio]-4-pteridinyl]amino]-1-propanol, (2R)-2-[[7-amino-2-[[(3-chloro-4-methoxyphenyl)methyl]thio]-4-pteridinyl]amino]-1-propanol, (2R)-2-[[7-amino-2-[[(3-chlorophenyl) methyl]thio]-4-pteridinyl]amino]-1-propanol, (2R)-2-[[7-amino-2-[[(5-methyl-2-furanyl)methyl]thio]-4-pteridinyl]amino]-1-propanol, (2R)-2-[[7-amino-2-[(2-thienylmethyl)thio]-4-pteridinyl]amino]-1-propanol, (2R)-2-[[7-amino-2-[[(2-fluoro-4-methoxyphenyl)methyl]thio]-4-pteridinyl]amino]-1-propanol, (2R)-2-[[7-amino-2-[[(3-chloro-2-fluorophenyl)methyl]thio]-4-pteridinyl]amino]-1-propanol, and their pharmaceutically acceptable salts.

5. A process for the preparation of a compound of formula (I) as defined in claim 1 which comprises:
(a) treating a compound of formula (II):

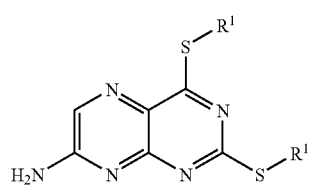

(II)

wherein R$^1$ is defined as in formula (I) with an amine R$^2$R$^3$NH and optionally thereafter forming a pharmaceutically acceptable salt.

6. A compound of formula (II)

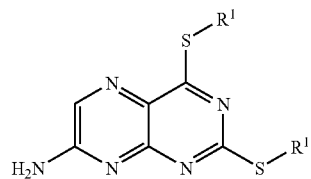

where R$^1$ represents a C$_3$–C$_7$ carbocyclic, C$_1$–C$_8$ alkyl, C$_2$–C$_6$ alkenyl or C$_2$–C$_6$ alkynyl group, each of the groups being optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$ or an aryl or heteroaryl group, both of which may be optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$ —SO$_2$NR$^5$R$^6$, —NR$^8$SO$_2$R$^9$, C$_1$–C$_6$ alkyl or trifluoromethyl groups R$^4$ represents hydrogen, C$_1$–C$_6$ alkyl or a phenyl group the latter two of which may be optionally substituted by one or more substituent groups independently selected from halogen atoms, phenyl, —OR$^{11}$ and —NR$^{12}$R$^{13}$ R$^5$ and R$^6$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or R$^5$ and R$^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —OR$^4$, —COOR$^{14}$, —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or C$_1$–C$_6$ alkyl, itself optionally substituted by one or more substituents independently selected from halogen atoms and —NR$^{15}$R$^{16}$ and —OR$^{17}$ groups;

R$^{10}$ represents a hydrogen atom or a C$_1$–C$_6$-alkyl or a phenyl group, the latter two of which may be optionally substituted by one or more substituent groups independently selected from halogen atoms, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ independently represents a hydrogen atom or a C$_1$–C$_6$, alkyl, or a phenyl group.

7. A pharmaceutical composition comprising a compound of formula (I), or a pharmaceutically acceptable salt thereof, as claimed in claim 1 in association with a pharmaceutically acceptable adjuvant, diluent or carrier.

8. A process for the preparation of a pharmaceutical composition as claimed in claim 7 which comprises mixing a compound of formula (I), or a pharmaceutically acceptable salt thereof, as claimed in claim 1 with a pharmaceutically acceptable adjuvant, diluent or carrier.

9. A process for the preparation of a pharmaceutical composition comprising mixing a compound of formula (I) or a pharmaceutically acceptable salt thereof, as claimed in claim 1, with a pharmaceutically acceptable adjuvant, diluent or carrier.

* * * * *